United States Patent [19]

Adams

[11] 4,323,067
[45] Apr. 6, 1982

[54] COMBINATION BREAST PUMP AND GAVAGE FEEDING APPARATUS AND METHOD

[76] Inventor: Frank H. Adams, 1246 Indiana Ave., Salt Lake City, Utah 84104

[21] Appl. No.: 917,552

[22] Filed: Jun. 21, 1978

Related U.S. Application Data

[63] Continuation-in-part of Ser. No. 807,773, Jun. 20, 1977, abandoned.

[51] Int. Cl.³ .............................................. A61M 1/06
[52] U.S. Cl. .................................... 128/281; 128/222
[58] Field of Search ............... 128/278, 280, 281, 282, 128/461, 222, 223, 235, 238, 300, 301, 352, 234; 119/14.47–14.53

[56] References Cited

U.S. PATENT DOCUMENTS

| 361,910 | 4/1887 | Tutton | 128/281 |
| 420,195 | 1/1890 | Graves et al. | 128/281 |
| 1,105,681 | 8/1914 | Muldenhauser | 119/14.47 |
| 1,238,390 | 8/1917 | Crittenden | 128/223 |
| 1,285,079 | 11/1918 | Eklundh et al. | 119/14.52 |
| 2,079,435 | 5/1937 | Dinesen | 119/14.49 |
| 2,208,089 | 7/1940 | Von Grolman | 128/281 |
| 3,645,262 | 2/1972 | Harrigan | 128/222 |
| 3,865,107 | 2/1975 | Barton | 128/214 C |
| 3,911,920 | 10/1975 | Susinn | 128/281 |

FOREIGN PATENT DOCUMENTS

| 524638 | 12/1953 | Belgium | 128/282 |
| 272561 | 3/1951 | Switzerland | 119/14.53 |
| 9747 | of 1894 | United Kingdom | 128/281 |
| 148449 | 12/1949 | United Kingdom | 128/280 |
| 493211 | 2/1976 | U.S.S.R. | 119/14.47 |

Primary Examiner—Robert W. Michell
Assistant Examiner—Arthur S. Rose
Attorney, Agent, or Firm—J. Winslow Young; H. Ross Workman; Rick D. Nydegger

[57] ABSTRACT

A combination breast pump and gavage feeding apparatus and method, the apparatus including means for applying suction to the nipple portion of a mammary gland while accommodating manual manipulation of the mammary gland for colostrum extraction and improved lactation. A pulse unit may also be included in the apparatus to impart the desired manipulatory action to at least the areola portion of the breast engaged by the breast pump. Air pressure and wall thickness and contour of the pulse unit are used in the pulse unit to provide the desired manipulatory action. The apparatus also includes interchangeable reservoir means for collecting the colostrum and/or milk therein for subsequent oral feeding and/or gavage feeding. A syringe barrel is configured as the reservoir means for the gavage feeding portion of the apparatus.

24 Claims, 11 Drawing Figures

COMBINATION BREAST PUMP AND GAVAGE FEEDING APPARATUS AND METHOD

This application is a continuation-in-part of my co-pending application for U.S. Pat. Ser. No. 807,773, filed June 20, 1977, now abandoned.

BACKGROUND

1. Field of the Invention

This invention relates to a breast pump and gavage feeding apparatus and method and, more particularly, to a breast pump for the application of suction against the nipple portion of the breast while accommodating manipulation of the remainder of the breast accompanied by selective mechanical manipulation of at least the areola portion of the breast.

2. Prior Art

Breast feeding has declined in all the technologically advanced societies of the world during this century and is also declining in developing countries. This decline in breast feeding is viewed as alarming for its deleterious effects on child health and resultant adverse effect on domestic and national economies. Numerous and complex factors have contributed to this decline. Accordingly, greater attention should be directed to the advantages of breast feeding. Additionally, attention should be directed also the the numerous immunological advantages of providing a newborn infant with a suitable supply of colostrum.

Breast milk is uniquely adapted to the nutritional requirements of an infant and is distinctly superior to any substitute which has been devised by nutritional scientists. Additionally, breast milk is free of the hazards associated with artifical feeding, characterized in disadvantaged societies particularly by malnutrition and gastroenteritis, and in affluent societies by obesity, allergic disorders, and metabolic derangements including tetany and hyper-osmolar dehydration.

Breast milk and, more particularly, colostrum has been found to contribute directly to the infant's immunological adaption to extrauterine life. Colostrum is the thin, milky fluid secreted by the mammary gland a few days before or after parturition. Colostrum is characterized by containing many colostrum corpuscles and by a high protein and immune content. It is currently believed that if the colostrum can be collected either a few days before or within a few days after parturition and subsequently fed to an infant, the infant's immunological defenses will be substantially benefitted. Infants born prematurely and/or requiring some form of isolation treatment are, therefore, deprived of the opportunity to obtain the colostrum through suckling. Accordingly, a previously collected and stored supply of colostrum could be advantageously administered to the infant by conventional feeding techniques and/or gavage feeding techniques.

Numerous documents in recent years have particularly expressed the need for intensifying activities relevant to the promotion of breast feeding. Additionally, many authorities are convinced that breast milk is the best food for infants and that breast feeding constitutes the most effective safeguard against malnutrition and infection in infancy, particularly in disadvantaged communities. It has also been proposed that breast feeding be advanced internationally through educational activities, curtailment of promotion of artificial feeding, improved facilities for working mothers who breast feed, improved devices for extracting and collecting breast milk and colostrum for subsequent feeding and/or gavage feeding, and improved devices for accommodating stimulation of lactation during periods when infant suckling is inadequate to suitably stimulate the appropriate lactation. The conventional breast pump consists of a bell-shaped housing having a frustoconical surface terminating in a suction bulb connection. The base of the bell-shaped housing is configured to receive a substantial portion of a breast while a suction bulb is used to impose a suction against the breast. A downwardly directed depression on the lower side of the bell-shaped housing serves as a reservoir for any milk extracted by suction from the breast.

To be useful in subsequent feeding operations, the milk thus collected must be poured into a suitable container such as a bottle or the like. Accordingly, milk collected by this technique is exposed to increased risk of contamination, spillage and the like. In addition, many women report that the rigid bell-shaped housing is uncomfortable, and in certain circumstances, painful to such a degree that further mechanical lactation with the device becomes impossible. Furthermore, the mere application of suction has been found to be inadequate for the purpose of suitably extracting breast milk. With the failure of the mechanical lactation techniques and inadequate or non-existant infant suckling, many women are discouraged from all further attempts at breast feeding.

In view of the foregoing, it would be a definite advantage in the art to provide a colostrum and/or breast milk extraction device which readily accommodates the stimulation and extraction of breast milk and, selectively, for subsequent conventional or gavage feeding of the collected fluids. It would be an even still further advancement in the art to provide a breast pump device which readily accommodates the manual manipulation and stimulation of the breast for improved lactation. Another advancement in the art would be to provide a breast pump apparatus wherein a plurality of interchangeable reservoir means for the purpose of adapting the extracted milk for storage and subsequent feeding. An even still further advancement in the art would be to provide a breast pump apparatus which readily accommodates a syringe-type reservoir for subsequent gavage feeding. Such an apparatus and method is disclosed and claimed in the present invention.

BRIEF SUMMARY AND OBJECTS OF THE INVENTION

The present invention provides a novel breast pump apparatus and method which accommodates manual manipulation of a breast while providing suitable suction against at least the nipple portion of the breast with an accompanying increased lactation. A plurality of interchangeable inserts adapt the breast pump for an improved sealing relationship with the nipple. A pulse unit may also be included with the breast pump to provide mechanical manipulation of at least the areola portion of the breast. A plurality of interchangeable reservoirs for the breast pump also adapt the extracted milk for subsequent storage, bottle feeding, and/or gavage feeding.

It is, therefore, a primary object of this invention to provide improvements in the art of breast pumps.

Another object of this invention is to provide an improved breast pump which readily accommodates the manual manipulation of the adjacent breast areas for improved stimulation of lactation while imposing a negative pressure on at least the nipple portion of the breast.

Another object of this invention is to provide an interchangeable pulse unit for the breast pump for selectively imparting a mechanical manipulatory action to at least the areola portion of the breast for increased lactation.

Another object of this invention is to provide an improved method for obtaining breast fluids.

Another object of this invention is to provide an improved apparatus for the collection and subsequent feeding of collected breast milk.

These and other objects and features of the present invention will become more fully apparent from the following description and appended claims taken in conjunction with the accompanying drawing.

DETAILED DESCRIPTION OF THE PREFERRED EMBODIMENTS

The invention is best understood by reference to the drawing wherein like parts are designated with like numerals throughout.

GENERAL DISCUSSION

Lactation is primarily a response to the lactogenic hormone of the pituitary gland but is also influenced by the nervous system through the stimulus of suckling. Suckling involves the application of suction to at least the apertures of the lactiferous ducts in the end of the nipple while, simultaneously, imparting an oral or mechanical manipulation to at least the nipple and surrounding areola portions of the breast. Additionally, manual manipulation of the breast is also known to stimulate lactation.

Continued lactation over a period of time is largely dependent upon the frequent and appropriate stimulation of the breast through suckling. Cessation of suckling over an extended period results in a temporary engorgement with milk of the mammary gland and is followed by a subsequent marked decrease in milk production. In view of the foregoing, it is customary for a nursing mother to mechanically extract milk whenever the infant is ill or otherwise unable to suitably supply the necessary suckling activity.

Figure 1:
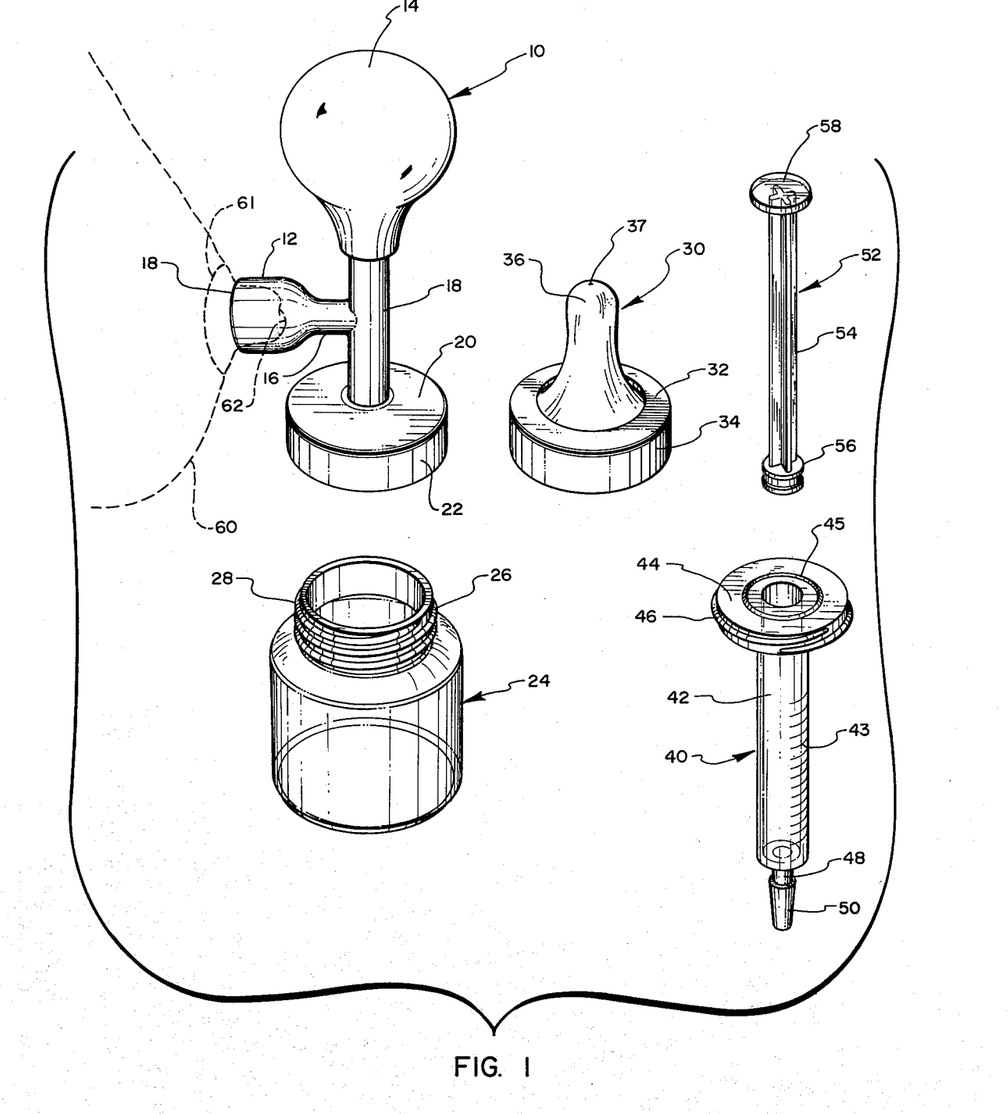
FIG. 1 is an exploded perspective view of one presently preferred embodiment of the breast pump apparatus of this invention showing different reservoir embodiments for the invention and including syringe apparatus for the subsequent gavage feeding of the collected breast fluids while maintaining maximum sterilization safety standards.

The Embodiment of FIG. 1

Referring now more particularly to FIG. 1, the breast pump apparatus of this invention is shown generally at 10 and includes a suction housing 12 and a squeeze bulb 14 interconnected in fluid connection therewith through conduits 16 and 18. Conduits 16 and 18 are interconnected in a "Tee" configuration and are in fluid communication with a coupling 20 on the lower end of conduit 18. Coupling 20 is configured as a conventional threaded cap having a downwardly depending rim 22 with an internal set of screw threads (not shown) to thereby serve as a coupling site for a plurality of reservoirs as will be discussed more fully hereinafter.

Housing 12 is configured as a cylindrical surface having an internal diameter adapted to fit over a nipple 62 (shown here in broken lines). The interior of the housing 12 (or an insert therein to be more fully described hereinafter) forms a seal with the nipple 62, the seal being indicated schematically at 17. The internal diameter of housing 12 may be regulated by inclusion of an insert (discussed more fully hereinafter with respect to FIGS. 2 and 3) to thereby accommodate variations in nipple diameters of nursing mothers. As noted, housing 12 may be provided with a plurality of interchangeable inserts for the purpose of selectively altering the internal diameter of housing 12 to thereby accommodate a sealing relationship with a nipple having a known external diameter. Customarily, such inserts will provide an internal diameter variation between 1 and 3 centimeters.

Figure 2:
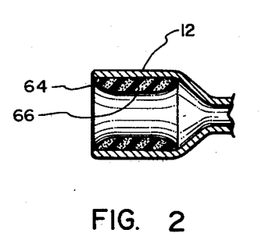
FIG. 2 is a cross section of a first preferred insert embodiment.

For example, and referring now more particularly to FIG. 2, a first preferred embodiment is shown herein as insert 64 and is engaged inside housing 12. The thickness of the annular ring of insert 64 is predetermined so as to provide an internal diameter 66 thereof which dimensionally corresponds with the external diameter of nipple 62 (FIG. 1) so as to provide an appropriate sealing relationship therewith. Insert 64 is fabricated from a soft, resilient material such as a closed-cell sponge material so as to resiliently engage nipple 62 (FIG. 1) in sealing relationship at seal 17 (FIG. 1).

Figure 3:
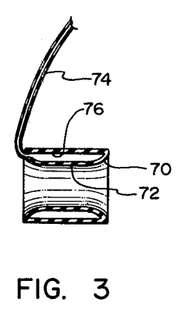
FIG. 3 is a cross section of a second preferred insert embodiment.

Referring now more particularly to FIG. 3, a second preferred embodiment is shown herein as insert 70. In particular, insert 70 is configured as a positive and/or negative pressure insert having an inflation tube 74 in fluid communication with a hollow lumen 76 inside insert 70. The external diameter of insert 70 is configurated so as to be tightly received in housing 12 (FIG. 1). The internal diameter 72 of insert 70 is suitably altered by inflation and deflation, selectively, so as to provide the appropriate seal 17 with nipple 62 (FIG. 1). Accordingly, insert 70 accommodates a greater range of nipple diameters for each specific insert whereas insert 64 (FIG. 2) must be replaced with an appropriate insert having the correct inside diameter 66 when dictated by differences in diameters of nipple 62 (FIG. 1). As will become further apparent, insert 70 may also be used to assist in extracting breast fluids.

Referring again to FIG. 1, it should be particularly noted that the seal 17 is formed around the nipple 62 and leaves a substantial portion of breast 60 and areola 61 exposed for manipulation as will be set forth more fully hereinafter.

One of the reservoirs suitable for the practice of this invention is shown herein as a bottle 24 having an upstanding neck 26 and a plurality of threads 28 thereon for the purpose of matingly engaging the dimensionally corresponding threads (not shown) inside rim 22 of coupling 20. Advantageously, bottle 24 and, correspondingly, the dimensions and threads (not shown) of coupling 20 are configured so that the bottle can be connected to the threads of a commercially available, four-ounce baby bottle cap or the like.

Bottle 24 is specifically configured to receive a conventional feeding nipple 30. Feeding nipple 30 is a conventional feeding nipple which is fabricated as a resilient bottle nipple 36 having at least one aperture 37 in the end thereof. Bottle nipple 36 is adapted to be secured to neck 26 of bottle 24 by a cap 32. Cap 32 includes a downwardly depending rim 34 having a plurality of threads (not shown) which are adapted to threadedly mate with threads 28 on neck 26.

An alternate reservoir embodiment is shown herein as a syringe reservoir 40. Syringe reservoir 40 includes a cylinderical syringe barrel 42 surmounted by a circular flange 44 at the upper end. Syringe barrel 42 terminates downwardly in a spout 48 on the lower end. Spout 48 is capped by a cap 50. Spout 48 is configured as a fitting which is adapted to be matingly received by a dimensionally corresponding fitting (not shown) in a gavage feeding tubing apparatus or the like (not shown). A plurality of indicia 43 are provided along the length of barrel 42 for the purpose of allowing the operator (not shown) to visually observe the volume of milk (not shown) therein. It will be apparent that the barrel 42 can also provide a writing surface on which such indentification as may be required can be written. Such information, for example, would include the name of the donar, the neonate, date of collection, and any other suitable information.

The outside diameter of circular flange 44 includes threads 46 which dimensionally correspond with the threads (not shown) of rim 22 of coupling 20 and rim 34 of cap 32. Additionally, circular flange 44 includes an annular ridge 45 for providing improved sealing relationship of circular flange 44 with coupling 20 and cap 32.

Syringe 40 may be any conventional syringe apparatus which has been specially configured to be matingly received by coupling 20. Importantly, syringe 40 is adapted to receive a plunger 52 therein for the purpose of allowing the operator (not shown) to forceably expel the collected milk therein (not shown) downwardly through spout 48. Plunger 52 includes a shaft 54 and a piston 56 on the lower end thereof. The external periphery of piston 56 sealingly mates with the internal surface of barrel 42 as in conventional syringes. The upper end of shaft 54 terminates in an enlarged button 58 which allows the operator (not shown) to use syringe 40 and plunger 52 in a conventional manner. Once the plunger 52 has been pushed into barrel 42 to start flow through spout 48, the flow may be maintained by gravity, if desired.

The Method

The method of this invention provides for the improved extraction of breast milk and/or colostrum either prior to or after parturition and readily provides for the storage and/or subsequent feeding of the collected fluids. In practicing the method of this invention, the operator (not shown) obtains the breast pump apparatus 10 and, selectively, adapts housing 12 to be engaged in sealing relationship with nipple 62. Where necessary, housing 12 is configured with a reduced, effective internal diameter by incorporating either insert 64 (FIG. 2) or insert 70 (FIG. 3) therein. The internal diameter 66 of insert 64 is selectively predetermined so as to provide the appropriate sealing relationship between insert 64 and nipple 62 (FIG. 1). Alternatively, insert 70 may be selectively inflated and deflated at the will of the operator to assist in milking while simultaneously providing the appropriate sealing relationship between insert 70 and nipple 62. Thus configured, breast pump apparatus 10 is completed by removably coupling therewith at coupling 20 a suitable reservoir such as bottle 24 or syringe 40.

In operation, the operator (not shown) compresses squeeze bulb 14 prior to placing housing 12 in sealing relationship at seal 17 over nipple 62. Thereafter squeeze bulb 14 is released causing a partial vacuum to be developed within the enclosure represented by conduits 16 and 18 and bottle 24 or syringe 40. With the suction thus applied to nipple 62, the operator (not shown) may suitably manipulate and/or massage the exposed area of breast 60 including areola 61. Accordingly, the milking apparatus 10 of this invention advantageously imposes the appropriate negative pressure on nipple 62 while allowing the operator to suitably manipulate or otherwise manually express milk and/or colostrum from breast 60.

The collection of milk (not shown) in bottle 24 or syringe 40 of breast pump apparatus 10 will result in a decrease in the partial vacuum imposed therein by squeeze bulb 14. Accordingly, breast pump 10, and more particularly housing 12, is removed from nipple 62 and squeeze bulb 14 again depressed after which housing 12 is again placed in sealing relationship at seal 17 over nipple 62. Thereafter, squeeze bulb 14 is released to again impose the appropriate negative pressure against nipple 62. Thereafter, the appropriate manual manipulation of breast 60 and areola 61 is continued for the further collection of fluids therefrom into bottle 24 or syringe 40. The foregoing procedure may be suitably continued for each of the right and the left breast until the appropriate lactic stimulation and/or fluid collection has been attained.

The collected fluids in bottle 24 or syringe 40 may be suitably treated and/or stored for subsequent feeding operations. For example, bottle 24 may be uncoupled from coupling 20 and capped with an appropriate feeding nipple 30. This is particularly advantageous for those circumstances wherein the nursing mother is unable to participate in the nursing of her infant and also in those instances where a wet nurse supplies breast milk for infant feeding. Additionally, the apparatus and method of this invention would be extremely useful for supplying supplemental quantities of breast milk for distribution to hospitals and organizations specializing in providing human milk for infants unable to digest other forms of milk and where the natural mother is unable to provide sufficient breast milk.

The use of syringe 40 as a milk collection reservoir is particularly advantageous since the apparatus of syringe 40 readily accommodates its being interconnected with the appropriate tubing for the gavage feeding of infants unable to be fed by use of the bottle nipple 30. For example, premature infants or infants experiencing some form of congenital defect may be advantageously supplied with the appropriate quantity of colostrum and/or breast milk through the gavage feeding apparatus of syringe 40. In these instances, the syringe 40 is uncoupled from coupling 20 and plunger 52 inserted therein. Cap 50 is removed from spout 48 and spout 48 is interconnected with a correspondingly dimensioned fitting (not shown) of a gavage feeding tubing set (not shown). Thereafter, plunger 52 is depressed by pushing button 58 toward circular flange 44 to start the flow of milk from syringe barrel 42 through spout 48.

As circumstances may dictate, bottle nipple 30 may be coupled with circular flange 44 to accommodate syringe 40 being used for conventional feeding in a manner comparable to the use of bottle 24 and feeding nipple 30. During such feeding cap 50 is removed to break any vacuum in the barrel and, to reduce the energy required of a baby to extract the milk from the barrel.

In addition to accommodating either gavage feeding or conventional bottle feeding, syringe 40 provides another advantage in that it reduces the reservoir volume. A reduced reservoir volume accommodates an increase in the negative pressure that can be developed by squeeze bulb 14. This may be particularly advantageous for collection of colostrum prior to parturition. Syringe 40 also has the additional advantage in that it readily lends itself to being capped and stored and provides a quickly ascertainable fluid volume indication by means of indicia 43 that will allow a continuous check on fluid that has been discharged.

Figure 4:
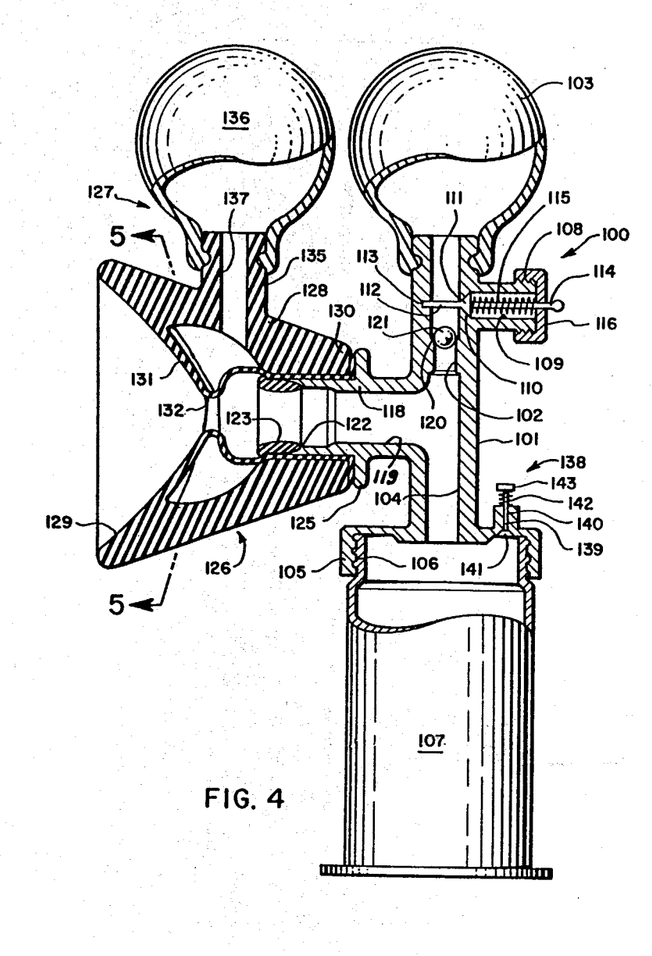
FIG. 4 is a side elevation view, partially broken away to show interior passages and valves, of an embodiment of the invention incorporating pulse unit means to manipulate a nipple.

Referring now to FIG. 4, a second preferred embodiment of the breast pump apparatus is shown as pump apparatus 100. Pump apparatus 100 includes a conduit 101 forming a passage 102 and having a squeeze bulb 103 mounted thereon in fluid communication therewith. An opposite extending passage 104 terminates in a flared cap 105 that is internally threaded at 106 to receive the threaded end of a container 107. Container 107 may be a conventional container, as illustrated or may be the baby bottle shown at 24 in FIG. 1, the syringe shown at 40 in FIG. 1, or of other suitable configuration.

A manually operated pressure relief valve 138 is carried by the flared lid 105 and is adapted to be operated to equalize pressures in and out of the container 107. The pressure relief valve 138 includes a stem 139 that projects through a bore 140 in the lid 105, a valve head 141 adapted to seat against and to close the bore 140, a spring 142 surrounding the stem 135, seated against the lid 105 and acting on a knob 143 to bias the stem and valve head 141 to close bore 140. As will become more apparent, the valve 138 will control the negative pressure in the reservoir when breast pump 100 is applied to a nipple (not shown) and can be manually pushed to equalize pressures inside and outside of the reservoir and to facilitate removal of the pump from the breast (not shown). In addition, the strength of spring 142 can be selectively predetermined to thereby adapt valve 138 as a pressure relief valve against excessive negative pressures in container 107.

A boss 108 projects from the side of conduit 101 and has a bore 109 that opens into passage 102 through a valve seat 110. A valve head 111 is arranged to engage valve seat 110 and to prevent flow therethrough. A guide stem 112 projects from one side of the valve head 111, across passage 102 and into a guide bore 113 formed in the wall of the passage 102. A spring stem 114 projects from the opposite side of the valve head so that a spring 115 placed thereover will rest against the valve head and will project past the end of stem 114 to engage a cap 116 threaded onto boss 108. A valve seat 120 is formed in the passage 102, between the passage 104 and the guide stem 112. A check valve, here shown as ball 121, is adapted to be gravity seated on the valve seat 120. The guide stem 112 then limits movement of the ball 121 in the passage 102.

A conduit 118 forms a "Tee" with tube 101. A bore 119 through the conduit intercepts the passage 104. The conduit 118 is stepped at 122 to provide for placement of an insert 123. As shown herein insert 123 is of the type previously described as insert 64 (FIG. 2), but it will be apparent that an inflatable insert of the type previously described as insert 70 (FIG. 3) could also be used merely by providing a hole (not shown) through the conduit 118 through which the inflating tube for the insert can be passed. Insert 123 is adapted to receive and resiliently engage a users nipple in the same manner as those inserts previously described.

A housing 128 serves as the primary structure for a pulse unit shown generally at 127 and is matingly received on conduit 118. Housing 126 is preferably made of a solid latex rubber, or the like, and includes a substantially rigid shell 128 that is formed by the thickness of material and is tapered inwardly from a large concave opening 129 to a smaller cylindrical portion 130 adapted to fit over the end of conduit 118 and to abut a collar 125. A boss 135 projects from the housing 126 to receive a squeeze bulb 136. A bore 137 through boss 135 and housing 126 interconnects the interior of the squeeze bulb with lumen 131a formed between membrane 131 and shell 128.

Shell 128 defines the outer portion of the concave opening 129 and a flexible and resilient membrane 131, preferably formed from the same flexible material such as latex rubber, or the like. Membrane 131 is, preferentially, fabricated and forms a spaced continuation of the concave opening 127 to a restricted opening 132 to thereafter fold back to be secured to the cylindrical portion 128 of the housing 126. The membrane 131 is of gradually decreasing thickness as it extends towards the opening 132. The membrane thereby forms a compartment of lumen with the rigid shell.

Figures 5, 6, 7:
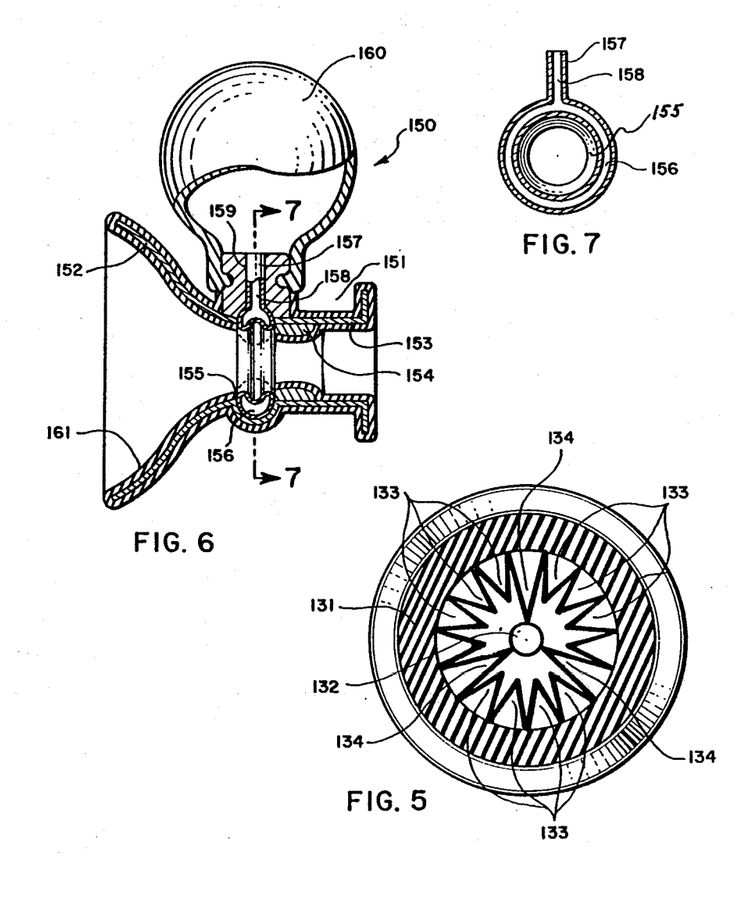
FIG. 5 is a cross section view, taken on the line 5—5 of FIG. 4.
FIG. 6 is a view, partly in elevation and partly in section, of another preferred pulse unit means for manipulating the nipple.
FIG. 7 is a cross-sectional view taken on the line 7—7 of FIG. 6 to better show the inflation member.
Figure 8:
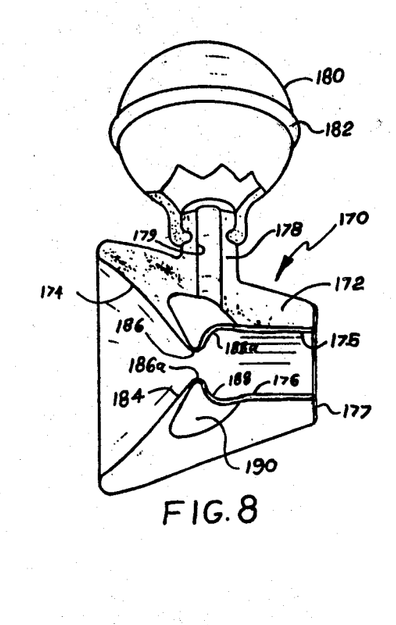
FIG. 8 is a view, partly in elevation and partly in section, of a pulse unit means for manipulating at least the nipple and/or areola portion of the breast in a first operative configuration.

As best seen in FIG. 5, the membrane 131 has a series of shorter, pointed fingers 133 formed therein as backing members that extend partially toward the restricted opening 132 and a number of longer, pointed fingers 134 that extend fully to the restricted opening 132. Fingers 133 and 134 are fabricated as an integral part or and on the internal face of membrane 131 inside lumen 131a. Importantly, Fingers 133 and 134 are fabricated as an increased wall thickness of membrane 131 to thereby impart a desired profile configuration to membrane 131 as will be set forth more fully hereinafter with respect to FIGS. 8–11.

In operation of the breast pump apparatus 100 shown in FIGS. 4 and 5, squeeze bulb 136 is preferably partially squeezed prior to its assembly on the boss 135 to create a partial vacuum in lumen 131a. The partial vacuum in lumen 131a serves to partially open restricted opening 132. The partial opening of restricted opening 132 accommodates receipt of a nipple (not shown) when concave opening 129 is engaged with a breast (not shown). With a breast engaged in concave opening 129, the nipple extends sealingly into and through the restricted opening 132 and may extend into insert 123 which functions as does the insert 64 (FIG. 2) and insert 70 (FIG. 3) previously described. Squeeze bulb 103 is then squeezed to force out the air therein. This air is blocked by check valve 121 but is allowed to escape through check valve 111 to the atmosphere. The bulb 103 is then released to create a negative pressure that will raise the check valve 121 from its seat 102 and thereby create a negative pressure in the container 107. This negative pressure then acts on the nipple through passage 104 and bore 119 to draw the breast, areola and nipple deeper into the restricted opening 132. Insert 123 thereby serves to sealingly engage the nipple (not shown) while helping hold the breast pump 100 in place.

With the breast and nipple (not shown) thereby engaged by breast pump apparatus 100, the operator (not shown) may selectively impart an appropriate mechanical, manipulatory action to the breast (not shown) by suitably inflating lumen 131a upon compression of squeeze bulb 136. The mechanical manipulatory action of membrane 131 against the breast and areola portions of the breast (not shown) will be more fully set forth hereinafter with respect to the description of FIGS. 8–11.

Removal of breast pump apparatus 100 from the breast (not shown) is readily accommodated by releasing the partial vacuum in container 107 by depressing knob 143 of pressure release valve 138 to allow atmospheric pressure into container 107 thereby breaking the partial vacuum therein. Simultaneously, squeeze bulb 136 may be relaxed thereby drawing a partial vacuum in lumen 131a to partially open restricted opening 132.

Referring now particularly to FIG. 6, another presently preferred embodiment of the pulse unit apparatus of this invention is shown herein as pulse unit 150 and includes a rigid shell 151 formed with a generally tubular portion 153 and opening into an outwardly flared, concave opening 152. The internal face of the outwardly flared, breast-receiving portion of the pulse unit engages and otherwise provides a sealing relationship with the breast (not shown) engaged thereby. Tubular portion 153 is dimensionally adapted to engage conduit 118 in abutment with collar 125 in the same manner as pulse unit 127 (FIG. 4).

Additionally, an insert 154 is included in pulse unit 150 and may be similarly configurated as insert 123 (FIG. 4), insert 64 (FIG. 2) and insert 70 (FIG. 3). Regardless of the insert used, insert 154 serves to sealingly engage a nipple (not shown) when pulse unit 150 is engaged with a breast (not shown).

With particular reference to FIG. 7 in combination with FIG. 6, a ring-shaped inflation member is adapted to be engaged within a recessed grove 156 in the wall of the tubular portion 153 between concave opening 152 and insert 154. Inflation member 155 includes an inflation tube 157 extending through a bore 158 in boss 159 and projecting from the tubular portion 153. Inflation tube 158 is in fluid communication with a squeeze bulb 160.

Preferentially, during assembly, the entire unit with the exception of squeeze bulb 160 and inflation member 155 is dipped in a latex material to provide a smooth coating of latex 161 and thereby eliminate pockets, grooves and the like, which might otherwise hinder sterilization by providing pockets for bacterial growth.

During assembly and after the pulse unit 151 has been dipped in latex, the squeeze bulb is partially depressed and attached to boss 159 so that a negative pressure is developed in inflation member 155 when squeeze bulb 160 is released. Importantly, inflation member 155 is collapsed along an internal wall thereof as shown in the cross section of FIG. 6 to accommodate a nipple (not shown) passing therethrough. Thereafter, squeeze bulb 160 may be suitably compressed to force air into lumen 156 of inflation member 155 thereby forming a constriction around the nipple (not shown). The constrictive action may be cyclically applied to impart a desired manipulatory action to the nipple. Additionally, the cyclical constriction of inflation member 155 prevents the reverse flow of milk from the engorged nipple (not shown) further facilitating extraction of the milk by the partial vacuum in container 107 (FIG. 4). In addition, the partial vacuum in container 107 (FIG. 4) also draws at least a portion of the areola within the confines of inflation member 155 thereby further accommodating the mechanical manipulation of at least the areola portion of the breast by the cyclical inflation of inflation member 155.

During operation, release of squeeze bulb 160 allows inflation member 155 to dilate as shown in FIG. 6 accommodating an inrush of milk from the breast into the nipple and areola portion of the breast (not shown). While under the continued application of a partial vacuum in container 107 (FIG. 4). The dilation of inflation member 155 also creates an area for expansion of the underlying breast tissue further assisting the inrush of milk to that portion of the breast. Subsequent inflation of inflatable member 155 to the position indicated by broken lines at 155a and, possibly beyond, imparts a constriction to the breast forceably expelling milk from the nipple also with the assistance of the partial vacuum in container 107 (FIG. 4).

Referring now to FIGS. 8–11, a pulse unit of this invention is shown generally at 170 and includes a housing 172 configurated with a conical, breast-receiving portion 174 at a leading face thereof and a cylindrical, conduit-receiving portion 176 on the reverse side. The conduit-receiving portion 176 is dimensionally adapted to be matingly engaged with conduit 118 (FIG. 4) to thereby provide breast pump apparatus 100 (FIG. 4) with the pulse unit 170. Clearly, of course, pulse unit 170 is the pulse unit alone and does not illustrate the various other features of breast pump apparatus 100 (FIG. 4) such as inserts 123 (FIG. 4) and the like.

Housing 172 is preferentially fabricated as a single-piece unit with a flexible membrane 184 formed as an integral part thereof. In particular, flexible membrane 184 includes a generally cylindrical portion terminating in an outwardly extending flange portion 177 and is sealed against the internal cylindrical section 176. Flange portion 177 is adapted to abut collar 125 (FIG. 4) and thereby assist in forming a sealing relationship between pulse unit 170 and conduit 118 (FIG. 4).

Membrane 184 is configurated substantially identical to membrane 131 (FIGS. 4 and 5) and may, selectively and advantageously, incorporate inwardly extending fingers 133 and 134 (FIG. 5). Fingers 133 and 134 (FIG. 5) are fabricated as an integral part of membrane 131 (FIGS. 4 and 5) and membrane 184 (not shown) so as to form a plurality of fingers having a predetermined wall thickness within membrane 184 thereby imparting a predetermined degree of stiffness to membrane 184 for the purposes that will be discussed more fully hereinafter. While fingers 133 and 134 (FIG. 5) are shown as sharply pointed fingers it should be clearly understood that any suitable geometric configuration for fingers 133 and 134 may be incorporated for the purposes set forth with respect to the practice of this invention.

Membrane 184 is configurated as a continuous, air impervious, flexible membrane having a leading face at the apex of conical surface 174 toward a restricted opening 186 and a reverse face 188. As can be readily seen from FIGS. 8-11, membrane 184 may be selectively fabricated with a selectively predetermined thickness varying between a thicker, leading face (as determined by its placement against a breast) and a thinner, inner face represented at 188. This variation in thickness, coupled with the fingers 133 and 134 (FIG. 5) provide for the preferential distension of membrane 184, as will be discussed more fully hereinafter. A hollow annulus beneath membrane 184 is fabricated as an inflatable lumen 190.

A boss 178 having a bore 179 therethrough provides fluid communication between a squeeze bulb 180 and lumen 190. Squeeze bulb 180 is configurated as a conventional squeeze bulb and may include a reinforcing rib 182 circumferentially surrounding squeeze bulb 180 to assist in providing the necessary resilience to the wall structure of squeeze bulb 180. Squeeze bulb 180 is sealed to boss 178 for the purposes that will be more fully understood hereinafter.

With the operation of squeeze bulb 180, membrane 184 has generally four operative configurations shown in each of FIGS. 8-11, respectively. For example, with particular reference to FIG. 8, during manufacture, squeeze bulb 180 is partially depressed prior to sealing squeeze bulb 180 to boss 178. Upon release of squeeze bulb 180, a partial vacuum is created in lumen 190 thereby drawing wall 188 inwardly causing restricted opening 186 to partially open to a configuration which will more readily accept a nipple and areola as set forth hereinbefore.

Figure 9:
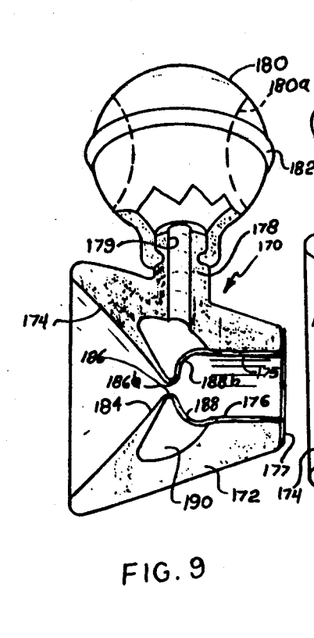
FIG. 9 is a view of the pulse unit means of FIG. 8 in a second operative configuration.

With particular reference to FIG. 9, depression of squeeze bulb 180 to the position shown in broken lines 180a releases the partial vacuum in lumen 190 allowing fingers 133 and 134 (FIG. 5) (which impart the desired resilience to membrane 184) to partially constrict constricted opening 186 to the position indicated at 186b. The return of the air pressure in lumen 190 to substantially that of the ambient allows fingers 133 and 134 (FIG. 5) to return to their substantially relaxed state while simultaneously constricting the orifice represented by constricted opening 186 as shown to the constricted opening shown at 186b. The reduction of the restricted opening 186 to the position indicated by position 186b constricts the underlying breast tissue thereby preventing the reverse flow of milk from the nipple and areola back into the breast.

Figures 10, 11:
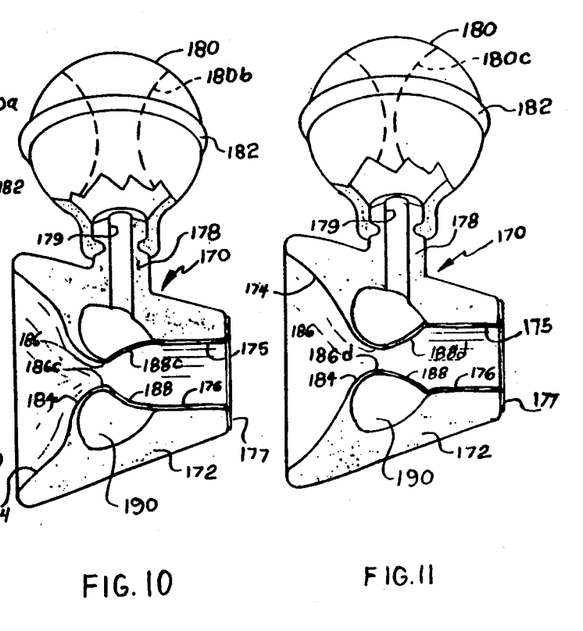
FIG. 10 is a view of the pulse unit means of FIG. 8 in a third operative configuration.
FIG. 11 is a view of the pulse unit means of FIG. 8 in a fourth operative configuration.

Referring now more particularly to FIG. 10, continued compression of squeeze bulb 180 to the position indicated in broken lines at position 180b provides a slight increase in pressure within lumen 190 forcing an outward distension of membrane 184 as shown. Squeezing squeeze bulb 180 to the position indicated in broken lines at 180b causes an increase in air pressure in lumen 190 overcoming the inherent resilience of fingers 133 and 134 (FIG. 5) on the reverse face of membrane 184 resulting in an outward distension of membrane 184. The outward distension of membrane 184 causes a mechanical manipulation and constriction of the underlying breast and areola portions of the breast. This outward distension is also coupled with a subsequent slight opening of restricted opening 186 to the position indicated at 186c thereby allowing additional milk to flow toward the nipple. Correspondingly, the inner wall 188 continues the milking action of the pulse unit 170 by constricting inwardly against the nipple (not shown) engaged by pulse unit 170.

With particular reference to FIG. 11, continued compression of squeeze bulb 180 to the position in dicated in broken lines at 180 causes a further distension of internal face 188 thereby completing the peristaltic pumping action of the pulse unit 170 by forcing the inner wall 188 to the position indicated at 188d.

Advantageously, the operation of pulse unit 170 as illustrated in each of the FIGS. 8-11 provides a desirable mechanical manipulatory action to the underlying breast tissue while simultaneously accommodating the imposition of a partial vacuum against the lactiferous ducts of the nipple (not shown). In this manner, the nervous system of the nursing women is suitably stimulated since the pulse unit 170 closely mimics the suckling action of an infant.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by a United States Letters Patent is:

1. A combination breast pump and gavage feeding apparatus comprising:

a conduit;

a suction means connected to the conduit and operable to impose a negative pressure in the conduit;

a housing interconnected in fluid communication with the conduit, the housing being dimensionally configurated to engage a nipple in sealing relationship;

a removable insert means for the housing, the insert means selectively altering the effective internal diameter of the housing, the insert means being configurated as a cylinder fabricated from a resilient material to accomodate sealing engagement between the housing and the nipple, the outside diameter of the insert means corresponding to the inside diameter of the housing and the inside diameter of the insert means being preselected to correspond to the outside diameter of the nipple thereby providing an improved sealing relationship between the nipple and the housing;

means to gently squeeze and manipulate the base of the nipple and surrounding aerola during application of negative pressure to the nipple comprising a pulse unit including a shell having a large concave opening adapted to receive a breast and connecting to a tubular opening adapted to be fixed to and to open into the housing; resilient means in the shell adapted to encircle and to engage the base of the nipple comprising a resilient, breast-engaging membrane and means for sequentially inflating and deflating the resilient, breast-engaging membrane, the resilient means further comprising inwardly projecting, pointed fingers forming backing members spaced around the resilient, breast-engaging membrane; and means for causing said resilient means to squeeze and manipulate the base of the nipple and the surrounding aerola to stimulate lactation;

a coupling means attached to the conduit in fluid communication therewith; and reservoir means removably coupled to the coupling means.

2. The apparatus defined in claim 1 wherein the reservoir means comprises a container having a threaded neck operable to receive a conventional hollow feeding nipple and cap combination.

3. The apparatus defined in claim 1 wherein the insert means is configurated as an inflatable member to accomodate being selectively inflated, and deflated for improved receipt of the nipple and sealing relationship between the housing and the nipple, the housing having an annular recess on an internal face thereof, the recess being adapted to receive the inflatable member therein in nesting relationship, the inflatable member having an initial negative pressure therein with the negative pressure retracting the insert means into the recess to further accomodate receipt of the nipple.

4. The apparatus defined in claim 1 wherein the coupling means comprises a threaded coupling.

5. The apparatus defined in claim 4 wherein the threaded coupling is configurated to receive a threaded neck of a conventional baby bottle.

6. The apparatus defined in claim 4 wherein the reservoir means comprises a syringe barrel having a threaded neck operable to be threadedly engaged to the threaded coupling.

7. The apparatus defined in claim 6 wherein the syringe barrel includes a threaded neck portion operable to receive a conventional feeding nipple and cap combination.

8. The apparatus defined in claim 6 wherein the syringe barrel has space thereon for identifying legends to be placed thereon.

9. The apparatus defined in claim 1 wherein the reservoir means comprises a syringe barrel having a spout and operable to receive a plunger to force fluid through the spout.

10. The apparatus as defined in claim 1 wherein the inwardly projecting pointed fingers comprise equiangularly spaced longer fingers and shorter fingers between the longer fingers.

11. The apparatus as defined in claim 1 wherein the resilient membrane is formed to have gradually decreasing thickness inwardly towards the ends of the fingers.

12. The apparatus as defined in claim 1 wherein the resilient means is of hollow ring-shaped configuration.

13. The apparatus as defined in claim 12 further including a latex coating over at least a portion of the unit except for the means for selectively inflating and deflating the resilient means.

14. The apparatus as defined in claim 1 wherein means for sequentially inflating and deflating the resilient means comprises a squeeze bulb.

15. The apparatus as defined in claim 1 wherein the suction means coupled to the housing and accomodating the imposition of a negative pressure on the nipple engaged in the housing comprises a squeeze bulb having a resilient wall.

16. A pulse unit comprising:

a housing and a shell connected to the housing, the shell having a large concave opening adapted to receive a breast and connecting to a tubular opening adapted to be fixed to and to open into the housing;

resilient means in the shell adapted to encircle and to engage the base of the nipple, the resilient means comprising a resilient, breast-engaging membrane having inwardly projecting pointed fingers spaced as backing members therearound;

the inwardly projecting pointed fingers comprising equiangularly spaced longer fingers and shorter fingers between the longer fingers, the fingers having relatively different lengths; and inflation means for sequentially inflating and deflating said resilient means to squeeze and manipulate the base of the nipple and the surrounding aerola to stimulate lactation.

17. The apparatus as defined in claim 16 wherein the means for sequentially inflating and deflating the resilient means comprises a squeeze bulb.

18. A breast manipulation apparatus comrising:

a collar adapted to receive at least the nipple and aerola portions of a breast in sealing relationship, the collar being configured with a hollow annulus corresponding to the nipple and aerola receiving portions of the collar, the wall of the hollow annulus facing the aerola and nipple portions of the breast being selectively fabricated from a resilient material having a plurality of inwardly projecting fingers fabricated as an integral part of the annulus wall, the fingers comprising equiangularly spaced longer fingers and shorter fingers between the longer fingers, the fingers having relatively different lengths and providing predetermined variations in thickness and size to thereby accommodate a predetermined manipulation of the aerola and nipple portions of the breast by using negative and positive pressure changes in the hollow annulus; and pressure change means for selectively altering pressure in the hollow annulus to accomodate predetermined movement of the wall of the annulus adjacent the aerola and nipple portions of the breast.

19. The breast manipulation apparatus of claim 18 wherein the collar comprises a housing having an external wall thickness which is greater than the internal wall thickness to thereby selectively inhibit the magnitude of external dimensional changes in the collar upon negative and positive pressure changes in the hollow annulus.

20. The breast manipulation apparatus of claim 18 wherein the annulus wall adjacent the nipple and aerola portions of the breast is fabricated to provide a first, nipple and aerola engagement profile at a first negative pressure condition in the hollow annulus, a second nipple and aerola engagement profile at a second, neutral pressure condition in the hollow annulus, and at least a third nipple and aerola engagement profile at a third, positive pressure condition in the hollow annulus.

21. The breast manipulation apparatus defined in claim 20 wherein the first engagement profile provides a relatively enlarged nipple-receiving opening surrounded by the hollow annulus.

22. The breast manipulation apparatus defined in claim 20 wherein the second engagement profile provides a relatively constricted nipple-receiving opening surrounded by the hollow annulus.

23. The breast manipulation apparatus defined in claim 20 wherein the third engagement profile provides a distended annulus wall to compress underlying breast tissue.

24. The breast manipulation apparatus defined in claim 20 wherein the annulus wall includes predetermined variations in the thickness of the annulus wall to thereby impart a predetermined directional movement of the annulus wall upon pressure changes in the hollow annulus.

* * * * *

UNITED STATES PATENT AND TRADEMARK OFFICE
CERTIFICATE OF CORRECTION

PATENT NO. : 4,323,067
DATED : Apr. 6, 1982
INVENTOR(S) : Frank H. Adams

It is certified that error appears in the above-identified patent and that said Letters Patent are hereby corrected as shown below:

Column 1, line 28, "the the numerous" should be --the numerous--

Column 1, line 50, "benefitted" should be --benefited--

Column 2, line 27, "non-existant" should be --non-existent--

Column 5, line 29, "cylinderical" should be --cylindrical--

Column 8, line 52, "of lumen" should be --or lumen--

Column 8, line 58, "or and on" should be --of and on--

Column 9, line 60, "grove" should be --groove--

Column 12, line 13, "in dicated" should be --indicated--

Column 14, lines 18, 25, 27, 29, 39, 46, 55, 57, 59, 61, "aerola" should be --areola--

Signed and Sealed this

Twenty-fourth Day of August 1982

|SEAL|

Attest:

GERALD J. MOSSINGHOFF

Attesting Officer     Commissioner of Patents and Trademarks